United States Patent
Lesieur et al.

(10) Patent No.: US 6,319,930 B1
(45) Date of Patent: Nov. 20, 2001

(54) SUBSTITUTED DIMERIC COMPOUNDS

(75) Inventors: Daniel Lesieur, Gondecourt; Said Yous, Lille; Carole Descamps-Francois, Hellemmes; François Lefoulon, Orleans; Gérald Guillaumet, Saint Jean le Blanc; Marie-Claude Viaud, Chambray les Tours; Caroline Bennejean, Charenton le Pont; Philippe Delagrange, Issy les Moulineaux; Pierre Renard, Le Chesnay, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/535,048

(22) Filed: Mar. 24, 2000

(30) Foreign Application Priority Data

Mar. 25, 1999 (FR) .................................. 99 03717

(51) Int. Cl.[7] .................... A61K 31/435; A61K 31/40; C07D 471/04; C07D 209/20
(52) U.S. Cl. ..................... 514/300; 514/414; 514/443; 514/469; 514/539; 546/113; 548/455; 549/58; 549/407; 549/467; 549/487; 560/28; 560/56; 564/56; 564/158; 564/220
(58) Field of Search ..................... 514/300, 414, 514/443, 469, 539; 546/113; 548/455; 549/58, 407, 467, 487; 560/28, 56; 564/56, 158, 220

(56) References Cited

PUBLICATIONS

Woolley, Biochemical Phrmacology, vol. 3, p. 51–59, 1959.*

* cited by examiner

Primary Examiner—Bernard Dentz
(74) Attorney, Agent, or Firm—The Firm of Hueschen and Sage; G. Patrick Sage

(57) ABSTRACT

The invention relates to compounds of formula (I):

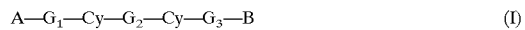

wherein:

A represents $NR^1C(Q)R^2$, $C(Q)NR^2R^3$ or $NR^1C(Q)NR^2R^3$,

B represents $NR^1C(Q)R^2$, $C(Q)NR^2R^3$, $NR^1C(Q)NR^2R^3$, $C(Q)OR^1$, $NR^1C(Q)OR^2$ or $NR^2R^3$, $G_1$ and $G_3$ represent an optionally substituted alkylene chain, Cy represents a ring structure

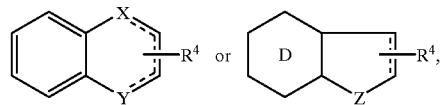

and G2 represents a chain

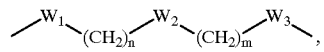

and medicinal products containing the same which are useful in treating or in preventing melatoninergic disorders.

24 Claims, No Drawings

SUBSTITUTED DIMERIC COMPOUNDS

FIELD OF THE INVENTION

The present invention relates to new substituted dimeric compounds having very valuable pharmacological properties in respect of melatoninergic receptors.

DESCRIPTION OF THE PRIOR ART

From the prior art dimeric naphthalenic structures are known (J. Chem. Soc., Dalton Trans., 1979, (10), pp. 1497–502) that have been studied for their coordination properties in metal complexes. Indole dimers have also been described for their "curare-like" activity (Khim.-Farm. Zh., 1984, 18(1), pp. 29–31).

BACKGROUND OF THE INVENTION

Owing to their novel structure, the compounds of the present invention are new and have pharmacological properties that are very valuable in respect of melatoninergic receptors.

Numerous studies in the last ten years have demonstrated the key role of melatonin (N-acetyl-5-methoxytryptamine) in many physiopathological phenomena and in the control of the circadian rhythm. Its half-like is quite short, however, owing to the fact that it is rapidly metabolised. Great interest therefore lies in the possiblity of providing the clinician with melatonin analogues that are metabolically more stable, have an agonist or antagonist character and that may be expected to have a therapeutic effect that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223) as well as for the treatment of Parkinson's disease (J. Neurosurg. 1985, 63, pp. 321–341) and Alzheimer's disease (Brain Research, 1990, 528, pp. 170–174). Those compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p 50; WO 97.04094). It has been possible, for various species, including mammals, for some of those receptors to be located and characterised. In order to be able to understand the physiological functions of those receptors better, it is of great advantage that specific ligands are available. Moreover, such compounds, by interacting selectively with one or other of those receptors, may be excellent medicaments for the clinician in the treatment of pathologies associated with the melatoninergic system, some of which have been mentioned above.

In addition to the fact that the compounds of the present invention are new, they show very strong affinity for melatonin receptors and/or selectivity for one or other of the melatoninergic receptor sub-types.

DETAILED DESCRIPTION OF THE INVENTION

The present invention relates more especially to compounds of formula (I):

$$A—G_1—Cy—G_2—Cy—G_3—B \quad\quad (I)$$

wherein:

A represents a grouping of formula

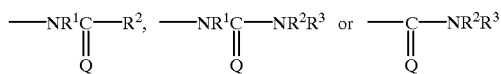

wherein

Q represents a sulphur or oxygen atom,

R$^1$, R$^2$ and R$^3$, which may be identical or different, represent a hydrogen atom or a group R$_a$ (wherein R$_a$ represents an unsubstituted or substituted linear or branched (C$_1$–C$_6$)alkyl group, an unsubstituted or substituted linear or branched (C$_2$–C$_6$)alkenyl group, an unsubstituted or substituted linear or branched (C$_2$–C$_6$)alkynyl group, an unsubstituted or substituted (C$_3$–C$_8$)-cycloalkyl group, an unsubstituted or substituted cycloalkyl-(C$_3$–C$_8$)alkyl (C$_1$–C$_6$)group in which the alkyl moiety is linear or branched, a polyhalo-(C$_1$–C$_6$)alkyl group in which the alkyl moiety is linear or branched, an aryl group, an aryl (C$_1$–C$_6$)alkyl group in which the alkyl moiety is linear or branched, an aryl(C$_2$–C$_6$)alkenyl group in which the alkenyl moiety is linear or branched, a heteroaryl group, a heteroaryl(C$_1$–C$_6$)alkyl group in which the alkyl moiety is linear or branched or a heteroaryl(C$_2$–C$_6$)alkenyl group in which the alkenyl moiety is linear or branched), or the groupings R$^2$ and R$^3$ form, with the nitrogen atom carrying them, a group selected from piperazinyl, piperidinyl and pyrrolidinyl, represents a grouping of formula

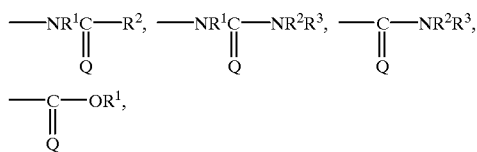

or

—NR$^2$R$^3$ wherein Q, R$^1$, R$^2$ and R$^3$ are as defined hereinbefore,

G$_1$ and G$_3$, which may be identical or different, represent a linear or branched alkylene chain having from 1 to 4 carbon atoms that is optionally substituted by one or more identical or different groups selected from hydroxy, carboxy, formyl, R$_a$, OR$_a$, COOR$_a$ and COR$_a$ (wherein R$_a$ is as defined hereinbefore), Cy represents
a ring structure of formula (II):

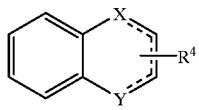

(II)

wherein:
X and Y, which may be identical or different, represent a sulphur, oxygen or carbon atom, or a CH or $CH_2$ group,
$R^4$ represents a hydrogen or halogen atom, or a $CF_3$, hydroxy, carboxy, formyl, amino, $NHR_a$, $NR_aR^1_a$, $NHCOR_a$, $CONHR_a$, $R_a$, $OR_a$, $COR_a$ or $COOR_a$ group (wherein $R_a$ is as defined hereinbefore and $R^1_a$ can have any of the meanings of $R_a$),
the symbol ---- means that the bonds are single or double, with the proviso that the valency of the atoms is respected,
wherein $G_2$ substitutes the benzene ring, and $G_1$ (and $G_3$ respectively) substitutes the ring containing X and Y,
or a ring structure of formula (III):

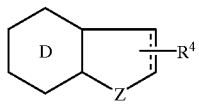

(III)

wherein:
Z represents a sulphur or oxygen atom, or a CH, $CH_2$, NH, $NSO_2Ph$ or $NR_a$ group (wherein $R_a$ is as defined hereinbefore),
D represents a benzene or pyridine ring,
$R^4$ is as defined hereinbefore,
the symbol ---- means that the bond is single or double, with the proviso that the valency of the atoms is respected,
wherein $G_2$ substitutes the D ring, and $G_1$ (and $G_3$ respectively) substitutes the ring containing Z,
it being understood that the two rings (Cy) of the compounds of formula (I) represent the same basic ring structure (indole/indole, naphthalene/naphthalene, benzofuran/ benzofuran, etc.), but the substituent $R^4$ may be different,
$G_2$ represents a chain of formula (IV):

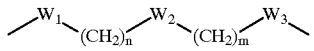

(IV)

wherein:
$W_1$, $W_2$ and $W_3$, which may be identical or different, represent a bond, an oxygen or sulphur atom, or a $CH_2$, $CHR_a$, NH or $NR_a$ group (wherein $R_a$ is as defined hereinbefore),
n represents an integer wherein $0 \leq n \leq 6$,
m represents an integer wherein $0 \leq m \leq 6$,
with the proviso that it is not possible to have two consecutive hetero atoms and that the chain of formula (IV) so defined may have one or more unsaturated bonds, wherein:
the compound of formula (I) cannot represent diethyl 2-(acetylamino)-2-{[5-({3-[2-(acetylamino)-3-ethoxy-2-(ethoxycarbonyl)-3-oxopropyl]-1H-indol-5-yl}methyl)-1H-indol-3-yl]methyl}malonate,
or N-{2-[5-({3-[2-(acetylamino)ethyl]-1H-indol-5-yl}methyl)-1H-indol-3-yl]-ethyl}acetamide,
"aryl" is understood to mean the groups naphthyl, phenyl and biphenyl,
"heteroaryl" is understood to mean any saturated or unsaturated mono- or bi-cyclic group containing from 5 to 10 atoms and containing from 1 to 3 hetero atoms selected from nitrogen, sulphur and oxygen,
it being possible for the "aryl" and "heteroaryl" groups to be substituted by one or more identical or different radicals selected from hydroxy, carboxy, linear or branched $(C_1-C_6)$alkoxy, linear or branched $(C_1-C_6)$alkyl, polyhalo-$(C_1-C_6)$-alkyl in which the alkyl moiety is linear or branched, formyl, cyano, nitro, amino, linear or branched $(C_1-C_6)$alkylamino, di-$(C_1-C_6)$alkylamino in which each alkyl moiety is linear or branched, and halogen atoms,
the term "substituted" applied to the terms "alkyl", "alkenyl" and "alkynyl" means that those groups are substituted by one or more identical or different radicals selected from hydroxy, linear or branched $(C_1-C_6)$alkoxy, polyhalo-$(C_1-C_6)$alkyl in which the alkyl moiety is linear or branched, amino, linear or branched $(C_1-C_6)$alkylamino, di-$(C_1-C_6)$alkylamino in which each alkyl moiety is linear or branched, and halogen atoms,
the term "substituted" applied to the terms "cycloalkyl" and "cycloalkylalkyl" means that the cyclic moiety of those groups is substituted by one or more identical or different radicals selected from hydroxy, linear or branched $(C_1-C_6)$alkoxy, polyhalo-$(C_1-C_6)$ alkyl in which the alkyl moiety is linear or branched, amino, linear or branched $(C_1-C_6)$alkylamino, di-$(C_1-C_6)$alkylamino in which each alkyl moiety is linear or branched, and halogen atoms,
their enantiomers and diastereoisomers, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred compounds of the invention are the compounds of formula (I) in which Cy represents a ring structure of formula (II), such as, for example, naphthalene or tetrahydronaphthalene, or of formula (III), such as, for example, indole, azaindole, benzothiophene or benzofuran.

Advantageously, the invention relates to the compounds of formula (I) wherein $G_2$ represents a single bond, or a grouping $—W_4—(CH_2)_p—W'_4—$ (wherein $W_4$ and $W'_4$, which may be identical or different, represent an oxygen or sulphur atom, or an NH or $NR_a$ group, and p represents an integer wherein $1 \leq p \leq 12$), such as, for example, the grouping $—O—(CH_2)_p—O—$ (wherein p is as defined hereinbefore), or a grouping of formula $-W_4-(CH_2)_{p'}-W'_4-(CH_2)_{p''}-W''_4-$ (wherein $W_4$, $W'_4$ and $W''_4$, which may be identical or different, represent an oxygen or sulphur atom, or an NH or $NR_a$ group, and p' and p" are two integers wherein $2 \leq p'+p'' \leq 12$), such as, for example, the grouping $-O-(CH_2)_{p'}-O-(CH_2)_{p''}-O-$ (wherein p' and p" are as defined hereinbefore).

Preferred substituents A and B of the invention are the groupings $NR^1C(Q)R^2$, $NR^1C(Q)NR^2R^3$ and $C(Q)NR^2R^3$, and more especially the groupings $NR^1COR^2$ and $CONR^2R^3$.

More especially still, the invention relates to the compounds of formula (I) which are:

N-(2-{7-[2-({8-[2-(acetylamino)ethyl]-2-naphthyl}oxy)ethoxy]-1-naphthyl}ethyl)-acetamide,
N-(2-{7-[3-({8-[2-(acetylamino)ethyl]-2-naphthyl}oxy)propoxy]-1-naphthyl}-ethyl)acetamide,
N-(2-{7-[4-({8-[2-(acetylamino)ethyl]-2-naphthyl}oxy)butoxy]-1-naphthyl}ethyl)-acetamide,
N-[2-(7-{[6-({8-[2-(acetylamino)ethyl]-2-naphthyl}oxy)hexyl]oxy}-1-naphthyl)-ethyl]acetamide,
N-[2-(7-{[8-({8-[2-(acetylamino)ethyl]-2-naphthyl}oxy)octyl]oxy}-1-naphthyl)-ethyl]acetamide,
N-[2-(7-{[10-({8-[2-(acetylamino)ethyl]-2-naphthyl}oxy)decyl]oxy}-1-naphthyl)-ethyl]acetamide,
N-[2-(7-{[5-({8-[2-(acetylamino)ethyl]-2-naphthyl}oxy)pentyl]oxy}-1-naphthyl)-ethyl]acetamide,
N-(2-{7-[4-({8-[2-(2-furoylamino)ethyl]-2-naphthyl}oxy)butoxy]-1-naphthyl}-ethyl)-2-furamide,
2-bromo-N-[2-(7-{4-[(8-{2-[(bromoacetyl)amino]ethyl}-2-naphthyl)oxy]-butoxy}-1-naphthyl)ethyl]acetamide,
N-[2-(7-{4-[(8-{2-[(cyclopropylcarbonyl)amino]ethyl}-2-naphthyl)oxy]-butoxy}-1-naphthyl)ethyl]cyclopropanecarboxamide,
N-(2-{7-[4-({8-[2-(3-butenoylamino)ethyl]-2-naphthyl}oxy)butoxy]-1-naphthyl}-ethyl)-3-butenamide,
N-(2-{7-[4-({8-[2-(acetylamino)ethyl]-7-methoxy-2-naphthyl}oxy)butoxy]-2-methoxy-1-naphthyl}ethyl)acetamide,
N-[2-(7-{2-[2-({8-[2-(acetylamino)ethyl]-2-naphthyl}oxy)ethoxy]ethoxy}-1-naphthyl)ethyl]acetamide,
tert-butyl 2-{7-[4-({8-[2-(acetylamino)ethyl]-2-naphthyl}oxy)butoxy]-1-naphthyl}ethyl carbamate,
N-{2-[7-(4-{[8-(2-aminoethyl)-2-naphthyl]oxy}butoxy)-1-naphthyl]ethyl}-acetamide hydrochloride
methyl {7-[4-({8-[2-(acetylamino)ethyl]-2-naphthyl}oxy)butoxy]-1-naphthyl}acetate,
{7-[4-({8-[2-(acetylamino)ethyl]-2-naphthyl}oxy)butoxy]-1-naphthyl}acetic acid,
N-(2-{7-[4-({8-[2-(acetylamino)ethyl]-5,6,7,8-tetrahydro-2-naphthalenyl}oxy)-butoxy]-1,2,3,4-tetrahydro-1-naphthalenyl}ethyl)acetamide,
N-{2-[5-(4-{[3-[2-(acetylamino)ethyl]-1-(phenylsulphonyl)-1H-indol-5-yl]-oxy}butoxy)-1-(phenylsulphonyl)-1H-indol-3-yl]ethyl}acetamide,
N-(2-{5-[4-({3-[2-(acetylamino)ethyl]-1H-indol-5-yl}oxy)butoxy]-1H-indol-3-yl}ethyl)acetamide,
N-(2-{5-[4-({3-[2-(acetylamino)ethyl]-1-benzofuran-5-yl}oxy)butoxy]-1-benzofuran-3-yl}ethyl)acetamide,
N-(2-{5-[4-({3-[2-(acetylamino)ethyl]-1-benzothien-5-yl}oxy)butoxy]-1-benzothien-3-yl}ethyl)acetamide,
N-(2-{5-[4-({3-[2-(acetylamino)ethyl]-1-methyl-1H-pyrrolo[3,2-b]pyridin-5-yl}oxy)butoxy]-1-methyl-1H-pyrrolo[3,2-b]pyridin-3-yl}ethyl)acetamide,
N-(2-{5-[4-({3-[2-(acetylamino)ethyl]-1-methyl-1H-pyrrolo[3,2-b]pyridin-5-yl}oxy)propoxy]-1-methyl-1H-pyrrolo[3,2-b]pyridin-3-yl}ethyl)acetamide,
N-[2-(7-{8-[2-(acetylamino)ethyl]-2-naphthyl}-1-naphthyl)ethyl]acetamide,
N-{2-[5-{3-[2-(acetylamino)ethyl]-1H-indol-3-yl}-1H-indol-3-yl]ethyl}acetamide.

The enantiomers, diastereoisomers and addition salts with a pharmaceutically acceptable acid or base of the preferred compounds of the invention form an integral part of the invention.

The present invention relates also to a process for the preparation of compounds of formula (I), characterised in that there is used as starting material a compound of formula (V):

$$A-G_1-Cy-OMe \qquad (V)$$

wherein A, $G_1$ and Cy are as defined for formula (I), which is subjected to demethylation using conventional agents, such as HBr, $AlCl_3$, $AlBr_3$, $BBr_3$ or Lewis acid/nucleophile binary systems, such as, for example, $AlCl_3/PhCH_2SH$ or $BBr_3/Me_2S$, to obtain a compound of formula (VI):

$$A-G_1-Cy-OH \qquad (VI)$$

wherein A, $G_1$ and Cy are as defined hereinbefore, which is converted, in conventional manner,
by the action of, for example, sodium N,N-dimethylthiocarbamate to the corresponding thiol of formula (VII):

$$A-G_1-Cy-SH \qquad (VII)$$

wherein A, $G_1$ and Cy are as defined hereinbefore,
or to the corresponding amine compound of formula (VIII):

$$A-G_1-Cy-NHR'_a \qquad (VIII)$$

wherein A, $G_1$ and Cy are as defined hereinbefore and $R'_a$ can have any of the meanings of $R_a$ as defined for formula (I) and can also represent a hydrogen atom, which compounds of formulae (VI), (VII) and (VIII) represent the compound of formula (IX):

$$A-G_1-Cy-W_4H \qquad (IX)$$

wherein $W_4$ represents an oxygen or sulphur atom, or an NH or $NR_a$ group (wherein $R_a$ is as defined hereinbefore), which compound of formula (IX) is condensed with:
a compound of formula (X):

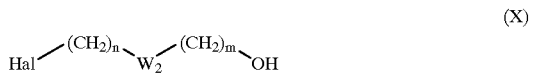

$$Hal \underset{}{\overset{(CH_2)_n}{\diagdown}} W_2 \underset{}{\overset{(CH_2)_m}{\diagdown}} OH \qquad (X)$$

wherein Hal represents a bromine, chlorine or iodine atom, and n, $W_2$ and m are as defined for formula (I), (with the proviso that it is not possible to have two consecutive hetero atoms and that the chain so defined may have one or more unsaturated bonds), or a compound of formula (XI):

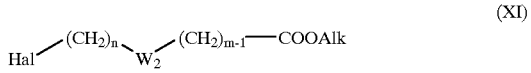
(XI)

wherein Hal, $W_2$, n and m are as defined hereinbefore and Alk represents an alkyl radical (with the proviso that it is not possible to have two consecutive hetero atoms and that the chain so defined may have one or more unsaturated bonds), followed by reduction, to yield a compound of formula (XII):

$$A-G_1-Cy-W_4-(CH_2)_n-W_2-(CH_2)_m-OH \qquad (XII)$$

wherein A, $G_1$, CY, $W_2$, $W_4$, n and m are as defined for formula (I) (with the proviso that it is not possible to have two consecutive hetero atoms in the $W_4-(CH_2)_n-W_2-(CH_2)_m-OH$ chain and that the chain so defined may have one or more unsaturated bonds), the hydroxyl function of which is converted in conventional manner to a leaving group, such as, for example, a mesylate, a tosylate, or a halogen compound, to yield a compound of formula (XII'):

$$A-G_1-Cy-W_4-(CH_2)_n-W_2-(CH_2)_m-E \qquad (XII')$$

wherein A, $G_1$, Cy, $W_4$, n, $W_2$ and m are as defined hereinbefore and E represents a mesyl or tosyl group or a halogen atom, which is subjected to the action of a compound of formula (XIII):

$$B-G_3-Cy-W'_4H \qquad (XIII)$$

wherein B, $G_3$ and Cy are as defined for formula (I) and $W'_4$ can have the same meanings as $W_4$ defined hereinbefore, to yield a compound of formula (I/a), a particular case of the compounds of formula (I):

$$A-G_1-Cy-W_4-(CH_2)_n-W_2-(CH_2)_m-W'_4-Cy-G_3-B \qquad (I/a)$$

wherein A, $G_1$, Cy, $W_4$, n, $W_2$, m, $W'_4$, $G_3$ and B are as defined hereinbefore, (which compounds of formula (I/a) wherein the groupings $A-G_1-Cy-W_4-$ and $W'_4-Cy-G_3-B$ are identical can be obtained directly from a compound of formula (IX) which is condensed, in a basic medium, with a compound of formula (X'):

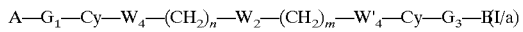
(X')

wherein Hal, n, m and $W_2$ are as defined hereinbefore), or converted using, for example, phenyl bis(trifluoromethanesulphonimide) in a basic medium to the corresponding trifluoromethanesulphonate of formula (XIV):

$$A-G_1-Cy-OSO_2CF_3 \qquad (XIV)$$

wherein A, $G_1$ and Cy are as defined hereinbefore, which is subjected, under conditions of catalysis by a suitable palladium compound, to the action of a boric acid compound $(R_bB(OH)_2)$ or of a tin compound $(R_bSnBu_3)$ (wherein $R_b$ represents a grouping of formula (XV):

$$B-G_3-Cy-W_3-(CH_2)_m-W_2-(CH_2)_n-CH_2- \qquad (XV)$$

wherein B, $G_3$, Cy, $W_3$, m, $W_2$ and n are as defined hereinbefore, with the proviso that it is not possible to have two consecutive hetero atoms in the $-W_3-(CH_2)_m-W_2-$ chain and that the chain so defined may have one or more unsaturated bonds), to yield a compound of formula (I/b), a particular case of the compounds of formula (I):

$$A-G_1-Cy-CH_2-(CH_2)_n-W_2-(CH_2)_m-W_3-Cy-G_3-B \qquad (I/b)$$

wherein A, $G_1$, Cy, n, $W_2$, m, $W_3$, Cy, $G_3$ and B are as defined hereinbefore (with the proviso that it is not possible to have two consecutive hetero atoms in the $-W_2-(CH_2)_m-W_3-$ chain and that the chain so defined may have one or more unsaturated bonds), which compounds of formula (I/c), a particular case of the compounds of formula (I):

$$A-G_1-Cy-W_1-(CH_2)_n-W_2-(CH_2)_m-CH_2-Cy-G_3-B \qquad (I/c)$$

wherein A, $G_1$, Cy, $W_1$, n, $W_2$, m, $G_3$ and B are as defined hereinbefore (with the proviso that it is not possible to have two consecutive hetero atoms in the $-W_1-(CH_2)_n-W_2-$ chain and that the chain so defined may have one or more unsaturated bonds), are obtained according to a similar procedure starting from a compound of formula (XIV'):

$$B-G_3-Cy-OSO_2CF_3 \qquad (XIV')$$

wherein B, $G_3$ and Cy are as defined hereinbefore, or is treated, under coupling conditions using, for example, nickel or palladium compounds, with a compound of formula (XIV') to yield a compound of formula (I/d), a particular case of the compounds of formula (I):

$$A-G_1-Cy-Cy-G_3-B \qquad (I/d)$$

wherein A, $G_1$, Cy, $G_3$ and B are as defined hereinbefore, the totality of the compounds (I/a) to (I/d) constituting the compounds of formula (I) which may be purified, if desired, by a conventional purification technique, are separated, where appropriate, into their isomers according to a conventional separation technique, and converted, if necessary, into addition salts thereof with a pharmaceutically acceptable acid or base.

The compounds of formula (V) are readily accessible to the person skilled in the art according to methods described in the literature.

The compounds of the invention and the pharmaceutical compositions containing them have proved to be useful in the treatment of disorders of the melatoninergic system.

The invention relates also to compounds of formula (XII"):

$$A-G_1-Cy-W_4-(CH_2)_n-W_2-(CH_2)_m-E' \qquad (XII")$$

wherein A, $G_1$, Cy, $W_4$, n, $W_2$ and m are as defined hereinbefore and E' represents a hydroxyl group or a halogen atom (fluorine, chlorine, bromine or iodine), with the proviso that
when Cy represents a naphthalene, and when simultaneously $G_1$—A represents a grouping —$(CH_2)_2$—$NR^1C(Q)R^2$ or —$(CH_2)_2$—$NR^1C(Q)NR^2R^3$ (wherein $R^1$, $R^2$ and $R^3$ are as defined hereinbefore), then the —$W_4$—$(CH_2)_n$—$W_2$—$(CH_2)_m$— chain cannot represent an —O—alkyl— chain, the compound of formula (XII") cannot represent N-{2-[5-(2-hydroxyethoxy)-1H-indol-3-yl]ethyl}acetamide, their enantiomers and diastereoisomers, and addition salts thereof with a pharmaceutically acceptable acid or base, as synthesis intermediates but also as compounds for use in the treatment of disorders associated with the melatoninergic system.

Pharmacological study of the compounds of the invention has in fact shown that they are atoxic, have a very high affinity for melatonin receptors and have substantial activities in respect of the central nervous system, and, in particular, therapeutic properties in respect of sleep disorders, anxiolytic, antipsychotic and analgesic properties, as well as properties in respect of microcirculation have been found, enabling it to be established that the compounds of the invention are useful in the treatment of stress, sleep disorders, anxiety, seasonal affective disorder, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention can be used in the treatment of sexual dysfunctions, that they have ovulation-inhibiting and immunomodulating properties and are capable of being used in the treatment of cancers.

The compounds will preferably be used in the treatment of seasonal affective disorder, sleep disorders, cardiovascular pathologies, insomnia and fatigue due to jetlag, appetite disorders and obesity.

For example, the compounds will be used in the treatment of seasonal affective disorder and sleep disorders.

The present invention relates also to pharmaceutical compositions comprising at least one compound of formula (I) on its own or in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration and especially tablets or dragées, sublingual tablets, sachets, paquets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication or any associated treatments, and ranges from 0.01 mg to 1 g per 24 hours in one or more administrations.

The following Examples illustrate the invention but do not limit it in any way. The following Preparations yield compounds of the invention or synthesis intermediates for use in the preparation of the invention.

Preparation 1: N-[2-(7-Hydroxy-1-naphthyl)ethyl]-acetamide

Under an inert atmosphere, 27.5 mmol of the boron tribromide/dimethyl sulphide complex are dissolved in 100 ml of dichloromethane and stirred for 15 minutes at room temperature. A solution of 13.7 mmol of N-[2-(7-methoxy-1-naphthyl)ethyl]acetamide in 50 ml of dichloromethane is added, and the reaction mixture is refluxed for 30 hours. After cooling, the reaction mixture is hydrolysed cautiously and the dichloromethane is removed by evaporation. The mixture is then extracted with ethyl acetate, and the combined organic phases are washed with an aqueous 1M potassium hydrogen carbonate solution. The organic phase is dried over magnesium sulphate and concentrated to yield the title compound. White solid.

Melting point: 125–126° C.

Preparations 2 to 19 are obtained by proceeding as for Preparation 1 starting from the appropriate substrate:

Preparation 2: N-Butyl-N'-[2-(7-hydroxy-1-naphthyl)ethyl]urea

Preparation 3: N-[2-(7-Hydroxy-1-naphthyl)ethyl]cyclopropanecarboxamide

Preparation 4: 4-(7-Hydroxy-1-naphthyl)-N-methylbutanamide

Preparation 5: N-[2-(7-Hydroxy-1-naphthyl)ethyl]-3-butenamide

Preparation 6: N-[2-(7-Hydroxy-3-phenyl-1-naphthyl)ethyl]acetamide

Preparation 7: N-[2-(5-Hydroxy-1-benzothiophen-3-yl)ethyl]butanamide

Preparation 8: 2,2,2-Trifluoro-N-[2-(5-hydroxy-1-benzothiophen-3-yl)ethyl]-acetamide Preparation 9: 4-(5-Hydroxy-1-benzofuran-3-yl)-N-methylbutanamide Preparation 10: N-[2-(5-Hydroxy-1-benzofuran-3-yl)ethyl]cyclopropanecarboxamide Preparation 11: N-[2-(5-Hydroxy-1-benzofuran-3-yl)ethyl]-N'-propylurea Preparation 12: N-{2-[5-Hydroxy-2-(3-methoxybenzyl)-1-benzofuran-3-yl]ethyl}acetamide Preparation 13: N-[2-(5-Hydroxy-1H-indol-3-yl)ethyl]-N'-propylthiourea Preparation 14: N-[2-(5-Hydroxy-1H-indol-3-yl)ethyl]cyclobutanecarboxamide Preparation 15: N-[2-(5-Hydroxy-1-methyl-1H-pyrrolo[2,3-b]pyridin-3-yl)ethyl]acetamide Preparation 16: N-[2-(5-Hydroxy-1-methyl-1H-pyrrolo[2,3-b]pyridin-3-yl)ethyl]-N'-propylurea Preparation 17: N-[2-(6-Hydroxy-3,4-dihydro-2H-chromen-4-yl)ethyl]acetamide Preparation 18: N-[(6-Hydroxy-2H-chromen-3-yl)methyl]butanamide Preparation 19: N-[(7-Hydroxy-1,4-benzodioxin-2-yl)methyl]-N'-propylurea Preparation 20: N-[2-(7-Mercapto-1-naphthyl)ethyl]benzamide Step A: N-[2-(7-Hydroxy-1-naphthyl)ethyl]benzamide The procedure is as for Preparation 1 starting from N-[2-(7-methoxy-1-naphthyl)ethyl]benzamide.

Step B: N-[2-(7-Mercapto-1-naphthyl)ethyl]benzamide

The product obtained in Step A (9 mmol) is added, with stirring, to a solution of potassium hydroxide (10 mmol) dissolved in 15 ml of water and 16 ml of tetrahydrofuran. The solution is cooled using a bath of ice and salt, and dimethylthiocarbamoyl chloride (9 mmol) dissolved in tetrahydrofuran (15 ml) is added dropwise with stirring. After stirring for half an hour while maintaining the cold temperature, the reaction mixture is extracted with chloroform. The organic phases are combined, dried over magnesium sulphate, filtered and then concentrated under reduced pressure. The residue is taken up in diphenyl ether (10 ml)

and refluxed for one hour under a nitrogen atmosphere. The diphenyl ether is removed by evaporation under reduced pressure until a solution of about 2 ml has been obtained. The 2 ml of distillate, which are still hot, are poured carefully into 50 ml of hexane to yield, after cooling, a solid which is isolated by filtration. The solid collected in that manner is added to a solution of potassium hydroxide (380 mg) dissolved in a water/methanol mixture (1 ml/10 ml). The solution is refluxed for 12 hours and then cooled and concentrated under reduced pressure. The residue is taken up in 20 ml of chloroform and extracted 3 times with water. The organic phase is dried over magnesium sulphate, filtered and concentrated under reduced pressure. The residue is chromatographed over silica gel to yield the title product.

Preparation 21: 2-Phenyl-N-[2-(5-mercapto-1-benzofuran-3-yl)ethyl]acetamide

The procedure is as for Preparation 20 starting from 2-phenyl-N-[2-(5-hydroxy-1-benzofuran-3 -yl)ethyl] acetamide.

Preparation 22: N-[2-(5-Amino-1-benzothiophen-3-yl) ethyl]cyclohexane-carboxamide Step A: N-[2-(5-Hydroxy-1-benzothiophen-3-yl)ethyl] cyclohexanecarboxamide The procedure is as for Preparation 1 starting from N-[2-(5-methoxy-1-benzothiophen-3-yl)ethyl] cyclohexanecarboxamide.

Step B: N-[2-(5-Bromo-1-benzothiophen-3-yl)ethyl] cyclohexanecarboxamide

Triphenylphosphine (10 mmol) and acetonitrile (70 ml) are poured into a 150 ml three-necked flask equipped with a dropping funnel, a cooler on top of which is mounted a tube filled with calcium chloride, and a mechanical stirrer. The solution is cooled using an ice-bath while maintaining stirring, and bromine (10 mmol) is added. When the addition is complete, the ice-bath is withdrawn and then the product obtained in Step A (8 mmol) is added. The reaction mixture is stirred at 60–70° C. until the starting material has disappeared. At the end of the reaction, the mixture is filtered, and then the filtrate is concentrated under reduced pressure. The residue is taken up in ethyl acetate, washed with water and then with a saturated potassium hydrogen carbonate solution, and once again with water, and then dried over magnesium sulphate and concentrated under reduced pressure. The residue is filtered over silica gel to yield the title product.

Step C: N-[2-(5-Iodo-1-benzothiophen-3-yl)ethyl] cyclohexanecarboxamide

A mixture of the product obtained in Step B (2 mmol), potassium iodide (30 mmol) and copper(I) iodide (10 mmol) in hexamethylphosphoramide (6 ml) is heated at 150–160° C. with stirring under a nitrogen atmosphere until a 90% conversion rate has been reached. Dilute hydrochloric acid is then added, followed by ether, and the mixture is then filtered to remove the insoluble copper(I) salts. The organic phase is separated off, washed with a solution of sodium sulphite and with water, dried over magnesium sulphate and evaporated to yield a residue which is chromatographed over silica gel to yield the title product.

Step D: N-[2-(5-Vinyl-1-benzothiophen-3-yl)ethyl] cyclohexanecarboxamide 15 mmol of the product obtained in Step C, 16 mmol of vinyl tributyltin and 0.43 mmol of tetrakis (triphenylphosphine)palladium, are heated at 110° C., with stirring, for 3 hours in 30 ml of N-methylpyrrolidinone. After removal of the solvent by evaporation, the residue is taken up in 20 ml of dichloromethane and treated with an aqueous 10% potassium fluoride solution. Extraction, concentration under reduced pressure and chromatography over silica gel yield the pure title product.

Step E : N-[2-(5-Formyl-1-benzothiophen-3-yl)ethyl] cyclohexanecarboxamide 1.10 g of osmium tetroxide in 2-methyl-2-propanol and then 8.70 g of sodium periodate are added at room temperature to a solution of 10 mmol of the product obtained in Step D in a mixture of 50 ml of dioxane and 25 ml of water. After stirring overnight at room temperature, the suspension is filtered and the filtrate is concentrated under reduced pressure. The resulting residue is taken up in dichloromethane. The organic phase is washed with water, dried and evaporated. The residue is purified by chromatography over silica gel to yield the title product.

Step F: 3-{2-[(Cyclohexylcarbonyl)amino]ethyl}-1-benzothiophene-5-carboxylic acid 2.7 g of potassium permanganate in 50 ml of an acetone/water mixture (50/50) are added at room temperature to a solution of 6.88 mmol of the product obtained in Step E in 30 ml of acetone. The solution is stirred for 2 hours at room temperature and then filtered. The filtrate is concentrated under reduced pressure and chromatographed over silica gel to yield the title product.

Step G: 3-{2-[(Cyclohexylcarbonyl)amino]ethyl}-1-benzothiophene-5-carboxylic acid chloride 5 mmol of the product obtained in Step F are dissolved in 40 ml of thionyl chloride. After stirring under an inert atmosphere for 1 hour, the thionyl chloride is removed by evaporation under reduced pressure to yield the title product.

Step H: N-[2-(5-Amino-1-benzothiophen-3-yl)ethyl] cyclohexanecarboxamide

A solution of the product obtained in Step G (20 mmol) in dichloromethane (30 ml) containing tetrabutylammonium bromide (20 mg) is cooled in an ice-bath. After the addition of sodium azide (25 mmol) dissolved in 5 ml of water, the solution is stirred vigorously at 0° C. for 2 hours. The organic phase is separated off, washed with water (2×5 ml) and dried over magnesium sulphate. After filtration, trifluoroacetic acid (30 mmol) is added and the solution is stirred under reflux for 60 hours. After cooling, the organic phase is washed with a saturated sodium hydrogen carbonate solution (2×5 ml) and concentrated under reduced pressure. The residue is then taken up in methanol (20 ml), and water (80 ml) and then potassium carbonate (30 mmol) are added. After stirring at room temperature for 20 hours, the reaction mixture is concentrated under reduced pressure to a volume of about 60 ml, and is then extracted 3 times with ether (3×50 ml). After drying over sodium sulphate, the organic phase is filtered and then evaporated under reduced pressure. The residue is chromatographed over silica gel to yield the title product.

Preparation 23: 2-(5-Amino-1-benzofuran-3-yl)-N-hexylacetamide

The procedure is as for Preparation 22.

Preparation 24: 8-[2-(Acetylamino)ethyl]-2-naphthyl trifluoromethanesulphonate 60 ml of triethylamine are added to a solution of 0.07 mol of the compound obtained in Preparation 1 in one litre of dichloromethane. The reaction mixture is refluxed until dissolution, and then 0.1 mol of phenyl bis (trifluoromethanesulphonimide) and 0.75 mol of potassium carbonate are added. After 4 hours' reflux, the mixture is washed with one litre of 1M sodium hydrogen carbonate and then with one litre of 1M hydrochloric acid. The organic phase is dried, concentrated and purified by chromatography over silica gel to yield the title product.

Preparation 25: 3-{2-[(Cyclopropylcarbonyl)amino]ethyl}-1-benzofuran-5-yl trifluoromethanesulphonate The procedure is as for Preparation 24 starting from the product obtained in Preparation 10.

Preparation 26: 3-[2-(Acetylamino)ethyl]-1-methyl-1H-pyrrolo[2,3-b]pyridin-5-yl trifluoromethanesulphonate The procedure is as for Preparation 24 starting from the compound obtained in Preparation 15.

Preparation 27: N-[2-(7-Hydroxy-1,2,3,4-tetrahydro-1-naphthalenyl)ethyl]-acetamide The procedure is as for Preparation 1 starting from N-[2-(7-methoxy-1,2,3,4-tetrahydro-1-naphthalenyl)ethyl] acetamide.

Melting point: 149–150° C.

Preparation 28: N-{2-[5-Hydroxy-1-(phenylsulphonyl)-1H-indol-3-yl]ethyl}acetamide Step A: N-{2-[5-Methoxy-1-(phenylsulphonyl)-1H-indol-3-yl]ethyl}acetamide Dissolve 5 g (21.5 mmol) of melatonin in 150 ml of dichloromethane. With stirring, add 3.41 g (84 mmol) of sodium hydroxide and 0.35 g (0.9 mmol) of tetrabutylammonium hydrogen sulphate. Cool the mixture in an ice-bath, and add 4.06 ml (31.5 mmol) of benzenesulphonyl chloride dropwise. After stirring overnight at room temperature, filter off the excess sodium hydroxide and the catalyst. Remove the solvent by evaporation in vacuo, and recrystallise the resulting solid.

Melting point: 140–141° C.

Step B: N-{2-[5-Hydroxy-1-(phenylsulphonyl)-1H-indol-3-yl]ethyl}acetamide

The procedure is as for Preparation 1 starting from the compound obtained in Step A.

Melting point: 205–206° C.

Preparation 29: N-[2-(5-Hydroxy-1-benzofuran-3-yl)ethyl] acetamide

The procedure is as for Preparation 1 starting from N-[2-(5-methoxy-1-benzofuran-3-yl)ethyl]acetamide.

Melting point: 140° C.

Preparation 30: N-[2-(5-Hydroxy-1H-indol-3-yl)ethyl] acetamide

The procedure is as for Preparation 1 starting from melatonin. Colourless oil.

Preparation 31: Tert-butyl 2-(7-hydroxy-1-naphthyl)ethyl carbamate

In a 100 ml round-bottomed flask, suspend 8-(2-aminoethyl)-2-naphthol hydrobromide (3 g, 1.12 mmol) in 30 ml of dichloromethane and add triethylamine (3.88 ml, 2.8 mmol). Cool the reaction mixture to 0° C. using an ice-bath, and add di-tert-butyl dicarbonate (2.2 g, 1 mmol) dissolved in 10 ml of dichloromethane dropwise. Stir the reaction mixture at room temperature for 4 hours. Wash the reaction mixture with an aqueous 0.5M hydrochloric acid solution and then with water. Dry the organic phase over magnesium sulphate and evaporate it under reduced pressure. Recrystallise the resulting residue from cyclohexane/toluene (1/10).

Melting point: 72–73° C.

Preparation 32: N-[2-(5-Hydroxy-1-methyl-1H-pyrrolo[3,2-b]pyridin-3-yl)ethyl]-acetamide The procedure is as for Preparation 1 starting from N-[2-(5-methoxy-1-methyl-1H-pyrrolo[3,2-b]pyridin-3-yl) ethyl]acetamide.

Preparation 33: 3-[2-(Acetylamino)ethyl]-1H-indol-5-yl trifluoromethanesulphonate The procedure is as for Preparation 24 starting from the compound obtained in Preparation 30.

Preparation 34: N-[2-(5-Hydroxy-1-benzothiophen-3-yl) ethyl]acetamide

The procedure is as for Preparation 1 starting from N-[2-(5-methoxy-1-benzothiophen-3-yl)ethyl]acetamide.

Melting point: 166–168° C.

Preparation 35: N-[2-(7-Hydroxy-2-methoxy-1-naphthyl) ethyl]acetamide

The procedure is as for Preparation 1 starting from N-[2-(2,7-dimethoxy-1-naphthyl)ethyl]acetamide.

EXAMPLE 1

N-(2-{7-[2-({8-[2-(Acetylamino)ethyl]-2-naphthyl}oxy)ethoxy]-1-naphthyl}ethyl)acetamide Step A: N-{2-[7-(2-Bromoethoxy)naphth-1-yl] ethyl}acetamide The compound obtained in Preparation 1 (0.009 mol) is dissolved in 20 ml of a mixture of dimethyl sulphoxide (6 ml) and butanone (14 ml). 0.027 mol of potassium carbonate and 0.036 mol of dibromoethane are added, and the mixture is heated at reflux for 48 hours. The reaction mixture is then cooled and poured into water. The aqueous phase is extracted with $Et_2O$, and then the organic phase is washed with water until the washing waters are neutral, and subsequently dried over magnesium sulphate and evaporated under reduced pressure. The resulting residue is purified by chromatography over silica gel (eluant: acetone/cyclohexane (2/8)) and recrystallised. White solid.

Melting point: 110–111° C.

Elemental microanalysis:

| % | C | H | N |
|---|---|---|---|
| Calculated: | 57.15 | 5.40 | 4.17 |
| Found: | 57.28 | 5.38 | 3.91 |

Step B: N-(2-{7-[2-({8-[2-(Acetylamino)ethyl]-2-naphthyl}oxy)ethoxy]-1-naphthyl}ethyl)acetamide In a 100 ml round-bottomed flask, 0.003 mol of the compound obtained in Preparation 1 and 0.003 mol of the compound obtained in Step A are dissolved in a mixture of 3 ml of dimethyl sulphoxide and 20 ml of butanone. 0.009 mol of potassium carbonate and one potassium iodide crystal are added and then the mixture is heated at reflux for 12 hours. The reaction mixture is then cooled and poured into 100 ml of water. The precipitate that forms is suctioned off and recrystallised. Beige solid.

Melting point: 220–222° C.

Elemental microanalysis:

| % | C | H | N |
|---|---|---|---|
| Calculated: | 71.69 | 6.61 | 5.57 |
| Found: | 72.03 | 6.60 | 5.53 |

EXAMPLE 2

N-{2-[7-(2-{[8-(2-{[(Butylamino)carbonyl] amino}ethyl)-2-naphthyl]oxy}ethoxy)-1-naphthyl] ethyl}acetamide The procedure is as for Example 1, in Step B replacing the naphthol obtained in Preparation 1 by the compound obtained in Preparation 2.

EXAMPLE 3

N-(2-{7-[2-({8-[2-(3-Butenoylamino)ethyl]-2-naphthyl}oxy]-1-naptyl}ethyl)-3-butenamide The procedure is as for Example 1, replacing the compound obtained in Preparation 1 by the compound obtained in Preparation 5.

EXAMPLE 4

N-[2-(7-{[2-({8-[2-(Acetylamino)ethyl]-2-naphthyl}oxy)ethyl]thio}-1-naphthyl)ethyl]benzamide The procedure is as for Example 1, in Step B replacing the naphthol obtained in Preparation 1 by the compound obtained in Preparation 20.

EXAMPLE 5

N-[2-(5-{[2-({3-[2-(Butylamino)ethyl]-1-benzothiophen-5-yl}oxy)ethyl]amino}-1-benzothiophen-3-yl)ethyl]cyclohexanecarboxamide The procedure is as for Example 1, replacing:

in Step A, the compound obtained in Preparation 1 by the compound obtained in Preparation 7, in Step B, the compound obtained in Preparation 1 by the compound obtained in Preparation 22.

EXAMPLE 6

N-(2-{7-[3-({8-[2-(Acetylamino)ethyl]-2-naphthyl}oxy)propoxy-1-naphthyl}ethyl)acetamide Step A: N-{2-[7-(3-Hydroxypropyloxy)naphth-1-yl]ethyl}acetamide In a 100 ml round-bottomed flask, 0.022 mol of the compound obtained in Preparation 1 is dissolved in 30 ml of dimethylformamide. 0.066 mol of potassium carbonate and 0.033 mol of 3-bromopropan-1-ol are added, and then the mixture is heated at 80° C. for 4 hours. The reaction mixture is cooled and poured into 100 ml of a 1M HCl solution. The aqueous phase is extracted 3 times with Et$_2$O and then the organic phase is dried over MgSO$_4$ and evaporated under reduced pressure. The title product is obtained by recrystallisation. White solid.

Melting point: 141–142° C.

Step B: 3-({8-[2-(Acetylamino)ethyl]-2-naphthyl}oxy)propyl methanesulphonate

In a 250 ml round-bottomed flask, the alcohol obtained in Step A is dissolved in 50 ml of dichloromethane, and 0.012 mol of triethylamine is added. The mixture is cooled in an ice/salt bath at −10° C., and then 0.012 mol of mesyl chloride is added dropwise with stirring with a magnetic stirrer. The reaction mixture is stirred at room temperature for 4 hours. 100 ml of water are then added, followed by extraction with CH$_2$Cl$_2$. The organic phase is washed with water, dried over MgSO$_4$ and evaporated under reduced pressure. The resulting oil is purified by chromatography over silica gel (eluant: acetone/cyclohexane (2/8)).

Step C: N-(2-{7-[3-({8-[2-(Acetylamino)ethyl]-2-naphthyl}oxy)propoxy]-1-naphthyl}ethyl)acetamide In a 100 ml round-bottomed flask containing 30 ml of methanol, 0.06 g of sodium is added in small portions. When the sodium has been completely used up, 0.0033 mol of the compound obtained in Preparation 1 is added, and the mixture is stirred for 20 minutes. The methanol is removed by evaporation under reduced pressure, the residue is taken up in 15 ml of DMF, and then 0.0027 mol of the compound obtained in Step B is added. The reaction mixture is then heated at reflux for 12 hours and subsequently cooled and poured into 100 ml of water and 10 ml of 3M HCl. After extraction with ethyl acetate, the organic phase is washed with a 10% sodium hydroxide solution and then with water. After drying over MgSO$_4$ and removal of the solvent by evaporation under reduced pressure, the title compound is obtained by recrystallisation. Beige solid.

Melting point: 101–103° C.

Elemental microanalysis:

| % | C | H | N |
| --- | --- | --- | --- |
| Calculated: | 74.67 | 6.87 | 5.18 |
| Found: | 74.31 | 6.87 | 5.15 |

EXAMPLE 7

N-(2-{7-[3-({8-[2-(Acetylamino)ethyl]-2-naphthyl}oxy)propoxy]-3-phenyl-1-naphthyl}ethyl)acetamide The procedure is as for Example 6, in Step C replacing the compound obtained in Preparation 1 by the compound obtained in Preparation 6.

EXAMPLE 8

N-Methyl-4-{7-[3-({8-[4-(methylamino)-4-oxopropyl]-2-naphthyl}oxy)-propoxyl-1-naphthyl}butanamide The procedure is as for Example 6, replacing the product of Preparation 1 by the compound obtained in Preparation 4.

EXAMPLE 9

N-(2-{5-[3-({3-[4-(Methylamino)-4-oxobutyl]-1-benzofuran-5-yl}oxy)-propoxy]-1-benzofuran-3-yl}ethyl)cyclopropanecarboxamide The procedure is as for Example 6, replacing:

in Step A, the compound of Preparation 1 by the compound of Preparation 9, in Step C, the compound of Preparation 1 by the compound of Preparation 10.

EXAMPLE 10

N-{2-[1-Methyl-5-(3-{[1-methyl-3-(2-{[(propylamino)carbonyl]amino}-ethyl)-1H-pyrrolo[2,3-b]pyridin-5-yl]oxy}propoxy)-1H-pyrrolo[2,3-b]pyridin-3-yl]ethyl}acetamide The procedure is as for Example 6, replacing:

in Step A, the compound of Preparation 1 by the compound of Preparation 15, in Step C, the compound of Preparation 1 by the compound of Preparation 16.

EXAMPLE 11

N-(2-{6-[3-({4-[2-(Acetylamino)ethyl]-3,4-dihydro-2H-chromen-6-yl}oxy)propoxy]-3,4-dihydro-2H-chromen-4-yl}ethyl)acetamide The procedure is as for Example 6, replacing the compound of Preparation 1 by the compound of Preparation 17.

EXAMPLE 12

N-(2-{7-[4-({8-[2-(Acetylamino)ethyl]-2-naphthyl}oxy)butoxy]-1-naphthyl}ethyl)acetamide Step A: Ethyl 4-({8-[2-(acetylamino)ethyl]-2-naphthyl}oxy)butanoate In a 100 ml round-bottomed flask, 0.022 mol of the compound obtained in Preparation 1 is dissolved in 50 ml of acetonitrile. 0.066 mol of potassium carbonate is added, and the reaction mixture is stirred at 80° C. for 30 minutes. 0.033 mol of ethyl 1-bromobutyrate are then added dropwise and the reaction mixture is stirred for 1 hour at 80° C. The acetonitrile is removed by evaporation under reduced pressure, and the residue is dissolved in a 1N HCl solution. After extraction with ethyl acetate, washing of the organic phase with water, drying over MgSO$_4$ and evaporation under reduced pressure, the title compound is purified by recrystallisation. Beige solid.

Melting point: 64–66° C.

Step B: N-{2-[7-(4-Hydroxybutyloxy)naphth-1-yl]ethyl}acetamide

In a 250 ml round-bottomed flask, the ester obtained in Step A (0.009 mol) is dissolved in 100 ml of anhydrous ether. 0.009 mol of lithium aluminium hydride is added in portions, and the reaction mixture is stirred for 6 hours at room temperature. The reaction mixture is then hydrolysed with a few drops of 1M NaOH, and the precipitate that forms is filtered off. The filtrate is dried over MgSO$_4$ and evaporated under reduced pressure. The resulting residue is precipitated from an Et$_2$O/petroleum ether mixture (1/1), suctioned off and recrystallised. White solid.

Melting point: 82–84° C.

Elemental microanalysis:

| % | C | H | N |
|---|---|---|---|
| Calculated: | 71.73 | 7.69 | 4.64 |
| Found: | 72.00 | 7.58 | 4.45 |

Step C: 4-({8-[2-(Acetylamino)ethyl]-2-naphthyl}oxy)butyl methanesulphonate

The procedure is as for Step B of Example 6 starting from the compound obtained in Step B.

Step D: N-(2-{7-[4-({8-[2-(Acetylamino)ethyl]-2-naphthyl}oxy)butoxy]-1-naphthyl}ethyl)acetamide The procedure is as for Step C of Example 6. Beige solid.

Melting point: 176–178° C.

Elemental microanalysis:

| % | C | H | N |
|---|---|---|---|
| Calculated: | 74.97 | 7.08 | 5.46 |
| Found: | 75.17 | 7.01 | 5.21 |

EXAMPLE 13

N-(2-{7-[4-({8-[4-(Methylamino)-4-oxobutyl]-2-naphthyl}oxy)butoxy]-1-naphthyl}ethyl)-3-butenamide The procedure is as for Example 12, in Step A replacing the compound of Preparation 1 by the compound of Preparation 4 and, in Step D, replacing the compound of Preparation 1 by the compound of Preparation 5.

EXAMPLE 14

N-(2-{7-[4-({8-[2-(Acetylamino)ethyl]-2-naphthyl}oxy)butoxy]-1-naphthyl}ethyl)cyclopropanecarboxamide The procedure is as for Example 12, in Step D replacing the compound of Preparation 1 by the compound of Preparation 3.

EXAMPLE 15

2,2,2-Trifluoro-N-[2-(5-{4-[(3-{2-[(2,2,2-trifluoroacetyl)amino]ethyl}-1-benzothiophen-5-yl)oxy]butoxy}-1-benzothiophen-3-yl)ethyl]acetamide The procedure is as for Example 12, replacing the compound of Preparation 1 by the compound of Preparation 8.

EXAMPLE 16

N-({6-[4-({3-[(Butyrylamino)methyl]-2H-chromen-6-yl}oxy)butoxy]-2H-chromen-3-yl}methyl)butanamide The procedure is as for Example 12, replacing the compound of Preparation 1 by the compound of Preparation 18.

EXAMPLE 17

N-[2-(7-{[6-({8-[2-(Acetylamino)ethyl]-2-naphthyl}oxy)hexyl]oxy}-1-naphthyl)ethyl]acetamide Step A: N-(2-{7-[(6-Hydroxyhexyl)oxy]-1-naphthyl}ethyl)acetamide The procedure is as for Step A of Example 6, replacing 3-bromopropan-1-ol by 6-bromohexan-1-ol. White solid.

Melting point: 58–61° C.

Elemental microanalysis:

| % | C | H | N |
|---|---|---|---|
| Calculated: | 72.91 | 8.41 | 4.25 |
| Found: | 73.22 | 8.17 | 4.02 |

Step B: 6-({8-[2-(Acetylamino)ethyl]-2-naphthyl}oxy)hexyl methanesulphonate

The procedure is as for Step B of Example 6. White solid.

Melting point: 66–67° C.

Step C: N-[2-(7-{[6-({8-[2-(Acetylamino)ethyl]-2-naphthyl}oxy)hexyl]oxy}-1-naphthyl)ethyl]acetamide The procedure is as for Step C of Example 6. White solid.

Melting point: 142–144° C.

Elemental microanalysis:

| % | C | H | N |
|---|---|---|---|
| Calculated: | 75.52 | 7.46 | 5.18 |
| Found: | 75.32 | 7.59 | 4.96 |

EXAMPLE 18

N-[2-(7-{[6-({8-[2-(Acetylamino)ethyl]-6-phenyl-2-naphthyl}oxy)-hexyl]oxy}-3-phenyl-1-naphthyl)ethyl]acetamide The procedure is as for Example 17, replacing the compound obtained in Preparation 1 by the compound obtained in Preparation 6.

EXAMPLE 19

2-Phenyl-N-{2-[5-({6-[(3-{2-[(2-phenylacetyl)amino]ethyl}-1-benzofuran-5-yl)thio]hexyl}thio)-1-benzofuran-3-yl]ethyl}acetamide The procedure is as for Example 17, replacing the compound of Preparation 1 by the compound of Preparation 21.

EXAMPLE 20

N-Hexyl-2-{5-[(6-{[3-(2-{[(propylamino)carbonyl]
amino}ethyl)-1-benzofuran-5-yl]oxy}hexyl)amino]-
1-benzofuran-3-yl}acetamide The procedure is as for Example 17, replacing:
in Step A, the compound of Preparation 1 by the compound of Preparation 23,
in Step C, the compound of Preparation 1 by the compound of Preparation 11.

EXAMPLE 21

N-{2-[5-[(6-{[3-[2-(Acetylamino)ethyl]-2-(3-
methoxybenzyl)-1-benzofuran-5-yl]oxy}hexyl)oxy]-
2-(3-methoxybenzyl)-1-benzofuran-3-yl]
ethyl}acetamide The procedure is as for Example 17, replacing the compound of Preparation 1 by the compound of Preparation 12.

EXAMPLE 22

N-{2-[5-({6-[(3-{2-[(Cyclobutylcarbonyl)amino]
ethyl}-1H-indol-5-yl)oxy]hexyl}oxy)-1H-indol-3-yl]
ethyl}cyclobutanecarboxamide The procedure is as for Example 17, replacing the compound of Preparation 1 by the compound of Preparation 14.

EXAMPLE 23

N-(2-{5-[(6-{[3-(2-{[(Propylamino)carbothioyl]
amino}ethyl)-1H-indol-5-yl]oxy}hexyl)oxy]-1H-
indol-3-yl}ethyl)cyclobutanecarboxamide The procedure is as for Example 17, replacing:
in Step A, the compound of Preparation 1 by the compound of Preparation 14,
in Step C, the compound of Preparation 1 by the compound of Preparation 13.

EXAMPLE 24

N'-Propyl-N-({7-[(6-{[3-({[(propylamino)carbonyl]
amino}methyl)-1,4-benzodioxin-6-yl]oxy}hexyl)
oxy]-1,4-benzodioxin-2-yl}methyl)urea The procedure is as for Example 17, replacing the compound of Preparation 1 by the compound of Preparation 19.

EXAMPLE 25

N-[2-(7-{8-[2-(Acetylamino)ethyl]-2-naphthyl}-1-
naphthyl)ethyl]-acetamide

Under nitrogen, 5.53 mmol of the compound obtained in Preparation 24, 1.94 mmol of dichlorobis (triphenylphosphine)nickel, 3.87 mmol of triphenylphosphine and 8.30 mmol of zinc are suspended in 20 ml of anhydrous DMF. After heating for 48 hours at 120° C. under nitrogen, the reaction mixture is concentrated and the resulting residue is partitioned between $CH_2Cl_2$ and 1M $NaHCO_3$. The organic phase is then dried over $Na_2SO_4$ and concentrated in vacuo. The title compound is obtained by chromatography over silica gel.

Melting point: 192.2–193.4° C.

EXAMPLE 26

N-(2-{5-(3-{2-[(Cyclopropylcarbonyl)amino]ethyl}-
1-benzofuran-5-yl)-1-benzofuran-3-yl}ethyl)
cyclopropanecarboxamide The procedure is as for Example 25, replacing the compound obtained in Preparation 24 by the compound obtained in Preparation 25.

EXAMPLE 27

N-{2-[5-{3-[2-(Acetylamino)ethyl]-1-methyl-1H-
pyrrolo[2,3-b]pyridin-5-yl}-1-methyl-1H-pyrrolo[2,
3-b]pyridin-3-yl]ethyl}acetamide The procedure is as for Example 25, replacing the compound obtained in Preparation 24 by the compound obtained in Preparation 26.

EXAMPLE 28

N-[2-(7-{[5-({8-[2-(Acetylamino)ethyl]-2-
naphthyl}oxy)pentyl]oxy}-1-naphthyl)ethyl]
acetamide Step A: Methyl 5-({8-[2-(acetylamino)ethyl]-2-naphthyl}oxy)pentanoate In a 250 ml round-bottomed flask, dissolve the compound obtained in Preparation 1 (4.6 g; 20 mmol) in 70 ml of acetonitrile. Add potassium carbonate (8.3 g; 60 mmol) and stir with a magnetic stirrer at reflux for 30 minutes. Then add methyl 5-bromovalerate (3.4 ml, 24 mmol) dropwise, and heat at reflux for 12 hours. Remove the acetonitrile by evaporation under reduced pressure. Take up the residue in water and extract 3 times with ethyl acetate. Wash the organic phase with an aqueous 1M hydrochloric acid solution, and then with water until the washing waters are neutral, dry over magnesium sulphate and evaporate under reduced pressure. Precipitate the resulting oil from a mixture of diethyl ether/petroleum ether (1/2). Suction off the precipitate that forms and recrystallise it from a mixture of toluene/cyclohexane (1/2). White solid.

Step B: N-(2-{7-[(5-Hydroxypentyl)oxy]-1-naphthyl)-ethyl}acetamide

In a 100 ml round-bottomed flask, dissolve the compound obtained in Step A (3.42 g, 10 mmol) in 50 ml of anhydrous tetrahydrofuran. Add lithium aluminium hydride (379.5 mg; 10 mmol) in small portions. Stir at room temperature for 6 hours. Hydrolyse the reaction mixture with 100 ml of an aqueous 1M hydrochloric acid solution. Extract the aqueous phase 3 times with dichloromethane. Dry the organic phase over magnesium sulphate and evaporate under reduced pressure. Use the resulting oil directly in the following Step.

Step C: 5-({8-[2-(Acetylamino)ethyl]-2-naphthyl}oxy) pentyl methanesulphonate

In a 250 ml round-bottomed flask, dissolve the compound obtained in Step B (3.15 g, 10 mmol) in 50 ml of dichloromethane and add triethylamine (1.6 ml; 12 mmol). Cool in an ice/salt bath at 0° C, and then add mesyl chloride (0.93 ml; 12 mmol) dropwise with stirring using a magnetic stirrer. Allow the reaction mixture to return to room temperature and stir for 5 hours. Add 100 ml of water and extract the aqueous phase 3 times with dichloromethane. Wash the organic phase with 3×20 ml of an aqueous 1M hydrochloric acid solution and then with water, dry over magnesium sulphate and evaporate under reduced pressure. Purify the resulting oil by chromatography over silica gel (eluant: acetone/cyclohexane (3/7)). Colourless oil.

Step D: N-[2-(7-{[5-({8-[2-(Acetylamino)ethyl]-2-naphthyl}oxy)pentyl]oxy}-1-naphthyl)ethyl]acetamide In a 100 ml round-bottomed flask containing 30 ml of methanol, add sodium (0.07 g 0.0030 at. g.) in small portions. When the sodium has been completely used up, add naphthol (0.82 g, 3.6 mmol). Stir using a magnetic stirrer for 20 minutes. Remove the methanol by evaporation under reduced pressure. Take up the resulting residue in 15 ml of dimethylformamide. Add the compound obtained in Step C (1.2 g, 3 mmol) and heat at reflux for 12 hours. Allow the reaction mixture to cool and pour it into a mixture of 100 ml of water and 10 ml of 3M hydrochloric acid. Extract the aqueous phase twice with ethyl acetate. Wash the organic phase with an aqueous 10% sodium hydroxide solution and then with water. Dry over magnesium sulphate and remove the ethyl acetate by evaporation under reduced pressure. Recrystallise the resulting solid residue from acetonitrile.

Melting point: 134–136° C.

EXAMPLE 29

N-[2-(7-{2-[2-({8-[2-(Acetylamino)ethyl]-2-naphthyl}oxy)ethoxy]-ethoxy}-1-naphthyl)ethyl] acetamide In a 100 ml round-bottomed flask, dissolve the compound obtained in Preparation 1 (1.14 g, 5 mmol) in 50 ml of acetonitrile. Add potassium carbonate (0.83 g, 6 mmol) and stir using a magnetic stirrer at reflux for 30 minutes. Then add bis(2-bromoethyl)ether (0.25 ml, 2 mmol) dropwise and heat at reflux for 12 hours. Remove the acetonitrile by evaporation under reduced pressure. Take up the resulting residue in an aqueous 1M sodium hydroxide solution. Filter off the resulting precipitate, wash it with water and recrystallise from acetonitrile and then from ethyl acetate.

Melting point: 135–138° C.

EXAMPLE 30

N-(2-{7-[4-({8-[2-(Acetylamino)ethyl]-5,6,7,8-tetrahydro-2-naphthalenyl}oxy)butoxy]-1,2,3,4-tetrahydro-1-naphthalenyl}ethyl)-acetamide In a 100 ml round-bottomed flask, dissolve the compound obtained in Preparation 27 (0.8 g, 3.4 mmol) in 50 ml of acetonitrile. Add potassium carbonate (0.57 g, 4.1 mmol) and stir using a magnetic stirrer at reflux for 30 minutes. Then add 1,4-dibromobutane (0.16 ml, 1.4 mmol) dropwise and heat at reflux for 12 hours. Remove the acetonitrile by evaporation under reduced pressure. Take up the resulting residue in an aqueous 1M sodium hydroxide solution. Filter off the resulting precipitate, wash it with water and recrystallise from acetonitrile.

Melting point:119–121° C.

EXAMPLE 31:

Tert-butyl 2-{7-[4-({8-[2-(acetylamino)ethyl]-2-naphthyl}oxy)butoxy]-1-naphthyl}ethyl carbamate In a 100 ml round-bottomed flask containing 30 ml of methanol, add sodium (0.07 g; 0.0030 at.g) in small portions. When the sodium has been completely used up, add the compound obtained in Preparation 31 (1 g, 3.6 mmol). Stir using a magnetic stirrer for 20 minutes. Remove the methanol by evaporation under reduced pressure. Take up the resulting residue in 15 ml of dimethylformamide. Add the compound obtained in Step C of Example 12 (1.1 g, 3 mmol) and heat at reflux for 12 hours. Allow the reaction mixture to cool and pour it into a mixture of 100 ml of water and 10 ml of 3M hydrochloric acid. Extract the aqueous phase twice with ethyl acetate. Wash the organic phase with an aqueous 10% sodium hydroxide solution and then with water. Dry over magnesium sulphate and remove the ethyl acetate by evaporation under reduced pressure. Recrystallise the resulting solid residue from toluene.

Melting point: 101–103° C.

EXAMPLE 32

N-{2-[5-(4-{[3-[2-(Acetylamino)ethyl]-1-(phenylsulphonyl)-1H-indol-5-yl]oxy}butoxy)-1-(phenylsulphonyl)-1H-indol-3-yl]ethyl}acetamide Dissolve 1 g (2.79 mmol) of the compound obtained in Preparation 28 in 20 ml of acetonitrile. With stirring, add 0.38 g (2.79 mmol) of potassium carbonate and 0.13 ml (1.11 mmol) of 1,4-dibromobutane. After refluxing overnight, pour the reaction mixture into 200 ml of water and ice. Filter off the precipitate, wash with ether, dry and recrystallise from a mixture of dioxane/water.

Melting point: 203–204° C.

EXAMPLE 33

N-(2-{5-[4-({3-[2-(Acetylamino)ethyl]1-benzofuran-5-yl}oxy)butoxy]-1-benzofuran-3-yl}ethyl) acetamide Dissolve 0.70 g (3.19 mmol) of the compound obtained in Preparation 29 in 20 ml of acetonitrile. Add 0.44 g (3.19 mmol) of potassium carbonate and 0.15 ml (1.28 mmol) of 1,4-dibromobutane with stirring. After refluxing overnight, pour the reaction mixture into 200 ml of water and ice. Filter off the precipitate, wash with ether, dry and recrystallise from toluene.

Melting point: 171 –172° C.

EXAMPLE 34

N-(2-{5-[4-({3-[2-(Acetylamino)ethyl]-1H-indol-5-yl}oxy)butoxy]-1H-indol-3-yl}ethyl)acetamide Dissolve 1 g (4.58 mmol) of the compound obtained in Preparation 30 in 20 ml of acetonitrile. Add 0.63 g (4.58 mmol) of potassium carbonate and 0.22 ml (1.83 mmol) of 1,4-dibromobutane with stirring. After refluxing overnight, pour the reaction mixture into 200 ml of water and ice. Filter off the precipitate, wash with acetone and dry.

Melting point: 208–209° C.

EXAMPLE 35

N-{2-[7-(4-{[8-(2-Aminoethyl)-2-naphthyl] oxy}butoxy)-1-naphthyl]ethyl}acetamide hydrochloride In a 100 ml flask, suspend the compound obtained in Example 31 in methanol. Bubble hydrogen chloride gas through until a clear phase has been obtained. Stir at room temperature for 5 hours. Suction off the precipitate that forms and recrystallise it from a mixture of acetonitrile/methanol (3/1).

Melting point: 188–189° C.

EXAMPLE 36

N-(2-{7-[4-({8-[2-(2-Furoylamino)ethyl]-2-naphthyl}oxy)butoxy]-1-naphthyl}ethyl)-2-furamide Step A: Tert-butyl 2-(7-{4-[(8-(2-[(tert-butoxycarbonyl) amino]ethyl}-2-naphthyl)-oxy]butoxy-}-1-naphthylethyl carbamate In a 100 ml round-bottomed flask, dissolve the compound obtained in Preparation 31 (5 mmol) in 50 ml of acetonitrile.

Add potassium carbonate (0.83 g, 6 mmol) and stir using a magnetic stirrer at reflux for 30 minutes. Then add 1,4-dibromobutane (0.37 ml, 2 mmol) dropwise and heat at reflux for 12 hours. Remove the acetonitrile by evaporation under reduced pressure. Take up the resulting residue in water and extract 3 times with ethyl acetate. Wash the organic phase with an aqueous 1M sodium hydroxide solution, with an aqueous 1M hydrochloric acid solution and then with water until the washing waters are neutral, dry it over magnesium sulphate and evaporate under reduced pressure. Recrystallise the resulting residue from methanol.

Melting point: 139–140° C.

Step B: 2-[7-(4-{[8-(2-Aminoethyl)-2-naphthyl]oxy}butoxy)-1-naphthyl]-ethylamine dihydrochloride In a 100 ml flask, suspend the compound obtained in Step A (2 g, 3.2 mmol) in methanol. Bubble hydrogen chloride gas through until a clear phase has been obtained. Stir at room temperature for 5 hours. Suction off the precipitate that forms and recrystallise it from acetonitrile.

Melting point: >240° C.

Step C: N-(2-{7-[4-({8-[2-(2-Furoylamino)ethyl]-2-naphthyl}oxy)butoxy]-1-naphthyl}ethyl)-2-furamide In a 250 ml flask, suspend the compound obtained in Step B (10 mmol) in a mixture of chloroform/water (3/2). Add potassium carbonate (50 mmol) with stirring. Cool the reaction mixture to 0° C. using an ice-bath, and then add 2-furoyl chloride (22 mmol). Maintain stirring at 0° C. for 1 hour at room temperature. Separate the two phases. Wash the organic phase with an aqueous 1M hydrochloric acid solution and then with water until the washing waters are neutral, dry it over magnesium sulphate and evaporate under reduced pressure. Recrystallise the resulting residue from acetonitrile.

Melting point: 179–180° C.

EXAMPLE 37

2-Bromo-N-[2-(7-{4-[(8-{2-[(bromoacetyl)amino]ethyl}-2-naphthyl)oxy]butoxy}-1-naphthyl)ethyl]acetamide The procedure is as for Example 36, replacing 2-furoyl chloride in Step C by bromoacetyl chloride.

Melting point: 155–157° C.

EXAMPLE 38

N-[2-(7-{4-[(8-{2-[(Cyclopropylcarbonyl)amino]ethyl}-2-naphthyl)-oxy]butoxy}-1-naphthyl)ethyl]cyclopropanecarboxamide The procedure is as for Example 36, replacing 2-furoyl chloride in Step C by cyclopropanecarbonyl chloride.

Melting point: 177–179° C.

EXAMPLE 39

N-(2-{7-[4-({8-[2-(3-Butenoylamino)ethyl]-2-naphthyl}oxy)butoxy]-1-naphthyl}ethyl)-3-butenamide The procedure is as for Example 36, replacing 2-furoyl chloride in Step C by 3-butenoyl chloride.

Melting point: 146–148° C.

EXAMPLE 40

N-(2-{5-[4-({3-[2-(Acetylamino)ethyl]-1-benzothien-5-yl}oxy)butoxy]-1-benzothien-3-yl}ethyl)acetamide In a 250 ml round-bottomed flask, dissolve the compound obtained in Preparation 33 in acetonitrile, add potassium carbonate and reflux for 30 minutes. Add 1,4-dibromobutane in fractions and heat at reflux for 15 hours. Evaporate to dryness, add water, filter and recrystallise the resulting precipitate from dioxane.

Melting point: 202–204° C.

EXAMPLE 41

N-[2-(7-{[8-({8-[2-(Acetylamino)ethyl]-2-naphthyl}oxy)octyl]oxy}-1-naphthyl)ethyl]acetamide In a 100 ml round-bottomed flask, dissolve the compound obtained in Preparation 1 (1.14 g, 5 mmol) in 50 ml of acetonitrile. Add potassium carbonate (0.83 g, 6 mmol) and stir using a magnetic stirrer at reflux for 30 minutes. Then add 1,8-dibromooctane (0.25 ml, 2 mmol) dropwise and heat at reflux for 12 hours. Remove the acetonitrile by evaporation under reduced pressure. Take up the resulting residue in an aqueous 1M sodium hydroxide solution. Filter off the resulting precipitate, wash it with water and recrystallise from acetonitrile.

Melting point: 137–139° C.

EXAMPLE 42

N-[2-(7-{[10-({8-[2-(Acetylamino)ethyl]-2-naphthyl}oxy)decyl]oxy}-1-naphthyl)ethyl]acetamide The procedure is as for Example 40, replacing 1,8-dibromooctane by 1,10-dibromodecane.

Melting point: 134–135° C.

EXAMPLE 43

Methyl {7-[4-({8-[2-(acetylamino)ethyl]-2-naphthyl}oxy)butoxy]-1-naphthyl}acetate Step A: 2-(7-Hydroxynaphth-1-yl)acetic acid In a 250 ml round-bottomed flask, dissolve 2-(7-methoxynaphth-1-yl)acetic acid in acetic acid. Add hydrobromic acid and reflux the reaction mixture for 4 hours. Remove the acetic acid and hydrobromic acid by evaporation under reduced pressure. Take up the solid in water and suction it off. Wash the precipitate with petroleum ether and recrystallise it from toluene.

Melting point: 151–152° C.

Step B: Methyl 2-(7-hydroxynaphth-1-yl)ethanoate

Dissolve the compound obtained in Step A in 100 ml of methanol. Cool the mixture in an ice-bath. Add thionyl chloride dropwise and maintain the reaction mixture at that temperature for 20 minutes after the addition. Leave for 1 hour at room temperature with stirring. Remove the methanol by evaporation under reduced pressure, and recrystallise the resulting solid from a mixture of toluene/cyclohexane (4/1).

Melting point: 115° C.

Step C: Methyl {7-[4-({8-[2-(acetylamino)ethyl]-2-naphthyl}oxy)butoxy]-1-naphthyl}acetate In a 250 ml round-bottomed flask, dissolve the compound in acetonitrile, add potassium carbonate and reflux the reaction mixture for 30 minutes. Add the bromine compound and maintain heating at reflux for 12 hours. The reaction mixture is suctioned off. The filtrate is evaporated under reduced pressure and the resulting oil is taken up in ether with stirring. Suction off the resulting precipitate and recrystallise it from methanol.

Melting point: 109–110° C.

EXAMPLE 44

{7-[4-({8-[2-(Acetylamino)ethyl]-2-naphthyl}oxy)butoxy]-1-naphthyl}acetic acid

In a 100 ml round-bottomed flask, dissolve the compound obtained in Example 43 in THF, and add methanol, water and sodium hydroxide. The reaction mixture is maintained at room temperature, with stirring, for 4 hours. Concentrate the solution, carry out hydrolysis and render acidic with concentrated hydrochloric acid. Suction off the resulting precipitate and recrystallise from a mixture of toluene/cyclohexane (4/1).

Melting point: 131–132° C.

EXAMPLE 45

N-(2-{7-[4-({8-[2-(Acetylamino)ethyl]-7-methoxy-2-naphthyl}oxy)-butoxy]-2-methoxy-1-naphthyl}ethyl)acetamide The procedure is as for Example 34 starting from the compound obtained in Preparation 35.

EXAMPLE 46

N-(2-{5-[4-({3-[2-(Acetylamino)ethyl]-1-methyl-1H-pyrrolo[3,2-b]-pyridin-5-yl}oxy)butoxy]-1-methyl-1H-pyrrolo[3,2-b]pyridin-3-yl}-ethyl)acetamide The procedure is as for Example 34 starting from the compound obtained in Preparation 32.

EXAMPLE 47

N-(2-{5-[4-({3-[2-(Acetylamino)ethyl]-1-methyl-1H-pyrrolo[3,2-b]-pyridin-5-yl}oxy)propoxy]-1-methyl-1H-pyrrolo[3,2-b]pyridin-3-yl}-ethyl)acetamide The procedure is as for Example 34 starting from the compound obtained in Preparation 32 and replacing 1,4-dibromobutane by 1,3-dibromopropane.

EXAMPLE 48

N-{2-[5-{3-[2-(Acetylamino)ethyl]-1H-indol-3-yl}-1H-indol-3-yl]ethyl}-acetamide

The procedure is as for Example 25, replacing the compound obtained in Preparation 24 by the compound obtained in Preparation 33.

Melting point: 237–238° C.

Pharmacological Study

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (the dose that causes the death of 50% of the animals) was evaluated and demonstrated the low toxicity of the compounds of the invention.

EXAMPLE B

Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin.

Bach experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

Melatonin $mt_1$ and $MT_2$ Receptor Binding Study

The $mt_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($IC_{50}$) to be determined.

Thus, the $IC_{50}$ values found for the compounds of the invention show binding for one or other of the $mt_1$ and $MT_2$ receptor sub-types, those values being $\leq 10 \mu M$.

EXAMPLE D

Action of the Compounds of the Invention on the Circadian Rhythms of Locomotive Activity of the Rat The involvement of melatonin in influencing the majority of physiological, biochemical and behavioural circadian rhythms by day/night alternation has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness) are evaluated.

Experimental Protocol

One-month-old male rats are subjected, as soon as they arrive at the laboratory, to a light cycle of 12 hours of light per 24 hours (LD 12:12). After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity:

influence of the light rhythm on the rhythms of activity, disappearance of the influence on the rhythms in permanent darkness, influence by the daily administration of the compound; transitory or durable effect.

A software package makes it possible:

to measure the duration and intensity of the activity, the period of the rhythm of the animals during free course and during treatment, possibly to demonstrate by spectral analysis the existence of circadian and non-circadian (for example ultradian) components.

Results

The compounds of the invention clearly appear to have a powerful action on the circadian rhythm via the melatoninergic system.

EXAMPLE E

Light/dark Cage Test

The compounds of the invention are tested on a behavioural model, the light/dark cage test, which enables the anxiolytic activity of the compounds to be revealed.

The equipment comprises two polyvinyl boxes covered with Plexiglas. One of the boxes is in darkness. A lamp is placed above the other box, yielding a light intensity of approximately 4000 lux at the centre of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

After administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Activity of the Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. The stimulation of the receptors can induce either vasoconstriction or dilation depending upon the arterial segment studied.

Protocol

One-month-old rats are accustomed to a light/dark cycle of 12h/12 h during a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 μM). A concentration/response curve is determined non-cumulatively by the addition of a concentration of the test compound to the pre-contracted segment. When the effect observed reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

EXAMPLE G

Pharmaceutical Composition: Tablets

| | |
|---|---|
| 1000 tablets containing a dose of 5 mg of N-(2-{7-[4-({8-[2-acetylamino)ethyl]-2-naphthyl}oxy)butoxy]-1-naphthyl}ethyl)acetamide (Example 12) | 5 g |
| Wheat starch | 20 g |
| Maize starch | 20 g |
| Lactose | 30 g |
| Magnesium stearate | 2 g |
| Silica | 1 g |
| Hydroxypropyl cellulose | 2 g |

We claim:

1. A compound selected from those of formula (I):

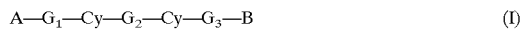

$$A\text{—}G_1\text{—}Cy\text{—}G_2\text{—}Cy\text{—}G_3\text{—}B \quad\quad (I)$$

wherein:

A represents a grouping of formula

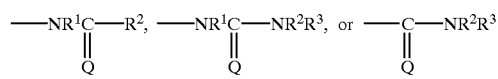

$$\text{—}NR^1C(\text{=}Q)\text{—}R^2, \quad \text{—}NR^1C(\text{=}Q)\text{—}NR^2R^3, \text{ or } \quad \text{—}C(\text{=}Q)\text{—}NR^2R^3$$

wherein:

Q represents sulphur or oxygen, $R^1$, $R^2$ and $R^3$, which may be identical or different, represent hydrogen or $R_a$ (wherein $R_a$ represents unsubstituted or substituted linear or branched ($C_1$–$C_6$)alkyl, unsubstituted or substituted linear or branched ($C_2$–$C_6$)alkenyl, unsubstituted or substituted linear or branched ($C_2$–$C_6$)alkynyl, unsubstituted or substituted ($C_3$–$C_8$)-cycloalkyl, unsubstituted or substituted cycloalkyl-($C_3$–$C_8$)alkyl ($C_1$–$C_6$) in which the alkyl moiety is linear or branched, polyhalo-($C_1$–$C_6$)alkyl in which the alkyl moiety is linear or branched, aryl, aryl($C_1$–$C_6$)alkyl in which the alkyl moiety is linear or branched, aryl($C_2$–$C_6$)alkenyl in which the alkenyl moiety is linear or branched, heteroaryl, heteroaryl($C_1$–$C_6$) alkyl in which the alkyl moiety is linear or branched, or heteroaryl($C_2$–$C_6$)alkenyl in which the alkenyl moiety is linear or branched), or $R^2$ and $R^3$ form, with the nitrogen atom carrying them, a group selected from piperazinyl, piperidinyl, and pyrrolidinyl, B represents a grouping of formula $$-NR^1-\underset{\underset{Q}{\|}}{C}-R^2, \quad -NR^1-\underset{\underset{Q}{\|}}{C}-NR^2R^3, \quad -\underset{\underset{Q}{\|}}{C}-NR^2R^3,$$

$$-\underset{\underset{Q}{\|}}{C}-OR^1,$$

$$-NR^1-\underset{\underset{Q}{\|}}{C}-OR^2,$$

or

—$NR^2R^3$, wherein Q, $R^1$, $R^2$ and $R^3$ are as defined hereinbefore, $G_1$ and $G_3$, which may be identical or different, represent a linear or branched alkylene chain having 1 to 4 carbon atoms that is optionally substituted by one or more identical or different groups selected from hydroxy, carboxy, formyl, $R_a$, $OR_a$, $COOR_a$ and $COR_a$ (wherein $R_a$ is as defined hereinbefore), Cy represents
a ring structure of formula (II):

(II)

wherein:
X and Y, which may be identical or different, represent sulphur, oxygen, carbon, or CH, or $CH_2$,
$R^4$ represents hydrogen, halogen, $CF_3$, hydroxy, carboxy, formyl, amino, $NHR_a$, $NR_aR^1_a$, $NHCOR_a$, $CONHR_a$, $R_a$, $OR_a$, $COR_a$, or $COOR_a$ (wherein $R_a$ is as defined hereinbefore and $R^1_a$ can have any of the meanings of $R_a$),
the symbol ——— means that the bonds are single or double, with the proviso that the valency of the atoms is respected,
wherein $G_2$ substitutes the benzene ring, and $G_1$ (and $G_3$ respectively) substitutes the ring containing X and Y,
or Cy represents a ring structure of formula (III):

(III)

wherein:
Z represents sulphur, oxygen, CH, $CH_2$, NH, $NSO_2Ph$, or $NR_a$ (wherein $R_a$ is as defined hereinbefore),
D represents a benzene or pyridine ring,
$R^4$ is as defined hereinbefore,
the symbol ——— means that the bond is single or double, with the proviso that the valency of the atoms is respected,
wherein $G_2$ substitutes the D ring, and $G_1$ (and $G_3$ respectively) substitutes the ring containing Z, it being understood that the two rings (Cy) of the compounds of formula (I) represent the same basic ring structure (indole/indole, naphthalene/naphthalene, benzofuran/benzofuran, etc.), but that the substituent $R^4$ may be different, $G_2$ represents a chain of formula (IV):

(IV)

$$-W_1-(CH_2)_n-W_2-(CH_2)_m-W_3-$$

wherein:
$W_1$, $W_2$ and $W_3$, which may be identical or different, represent a bond, oxygen, sulphur, $CH_2$, $CHR_a$, NH, or $NR_a$ (wherein $R_a$ is as defined hereinbefore),
n represents $0 \leq n \leq 6$,
m represents $0 \leq m \leq 6$,
with the proviso that it is not possible to have two consecutive hetero atoms and that the chain of formula (IV) so defined may have one or more unsaturated bonds,
wherein:
the compound of formula (I) cannot represent diethyl 2-(acetylamino)-2-{[5-({3-[2-(acetylamino)-3-ethoxy-2-(ethoxycarbonyl)-3-oxopropyl]-1H-indol-5-yl}methyl)-1H-indol-3-yl]methyl}malonate,
or N-{2-[5-({3-[2-(acetylamino)ethyl]-1H-indol-5-yl}methyl)-1H-indol-3-yl]-methyl}acetamide,
"aryl" is understood to mean naphthyl, phenyl, or biphenyl,
"heteroaryl" is understood to mean any saturated or unsaturated mono- or bi-cyclic group containing 5 to 10 atoms and containing 1 to 3 hetero atoms selected from nitrogen, sulphur, and oxygen,
it being possible for "aryl" and "heteroaryl" to be substituted by one or more identical or different radicals selected from hydroxy, carboxy, linear or branched ($C_1$–$C_6$)alkoxy, linear or branched ($C_1$–$C_6$)alkyl, polyhalo-($C_1$–$C_6$)alkyl in which the alkyl moiety is linear or branched, formyl, cyano, nitro, amino, linear or branched ($C_1$–$C_6$) alkylamino, di-($C_1$–$C_6$)alkylamino in which each alkyl moiety is linear or branched, and halogen,
the term "substituted" applied to the terms "alkyl", "alkenyl", and "alkynyl" means that those groups are substituted by one or more identical or different radicals selected from hydroxy, linear or branched ($C_1$–$C_6$)alkoxy, polyhalo-($C_1$–$C_6$)alkyl in which the alkyl moiety is linear or branched, amino, linear or branched ($C_1$–$C_6$)alkylamino, di-($C_1$–$C_6$) alkylamino in which each alkyl moiety is linear or branched, and halogen,
the term "substituted" applied to the terms "cycloalkyl" and "cycloalkylalkyl" means that the cyclic moiety of those groups is substituted by one or more identical or different radicals selected from hydroxy, linear or branched ($C_1$–$C_6$)alkoxy, polyhalo-($C_1$–$C_6$) alkyl in which the alkyl moiety is linear or branched, amino, linear or branched ($C_1$–$C_6$)alkylamino, di-($C_1$–$C_6$)alkylamino in which each alkyl moiety is linear or branched, and halogen,
its enantiomers and diastereoisomers, and addition salts thereof with a pharmaceutically-acceptable acid or base.

2. A compound of formula (I) according to claim 1 wherein Cy represents a ring structure of formula (II).

3. A compound of formula (I) according to claim 1 wherein Cy represents a naphthalene.

4. A compound of formula (I) according to claim 1 wherein Cy represents a ring structure of formula (III).

5. A compound of formula (I) according to claim 1 wherein Cy represents a benzothiophene or a benzofuran.

6. A compound of formula (I) according to claim 1 wherein Cy represents an indole.

7. A compound of formula (I) according to claim 1 wherein Cy represents an azaindole.

8. A compound of formula (I) according to claim 1 wherein $G_2$ represents a single bond.

9. A compound of formula (I) according to claim 1 wherein $G_2$ represents —$W_4$—$(CH_2)_p$—$W'_4$— wherein $W_4$ and $W'_4$, which may be identical or different, represent oxygen or sulphur or NH or $NR_a$, and p represents an integer wherein $1 \leq p \leq 12$.

10. A compound of formula (I) according to claim 1 wherein $G_2$ represents —O—$(CH_2)_p$—O— wherein p represents an integer wherein $1 \leq p \leq 12$.

11. A compound of formula (I) according to claim 1 wherein $G_2$ represents $W_4$—$(CH_2)_{p'}$—$W'_4$—$(CH_2)_{p''}$—$W''_4$— wherein $W_4$, $W'_4$ and $W''_4$, which may be identical or different, represent oxygen or sulphur or NH or $NR_a$, and p' and p" are integers wherein $2 \leq p'+p'' \leq 12$.

12. A compound of formula (I) according to claim 1 wherein $G_2$ represents —O—$(CH_2)_{p'}$—O—$(CH_2)_{p''}$—O— (wherein p' and p" are integers wherein $2 \leq p'+p'' \leq 12$).

13. A compound of formula (I) according to claim 1 wherein A and B, which may be identical or different, represent $NR^1COR^2$ or $CONR^2R^3$.

14. A Compound of formula (I) according to claim 1 which is selected from N-(2-{7-[2-({8-[2-(acetylamino)ethyl]-2-naphthyl}oxy)ethoxy]-1-naphthyl}ethyl)acetamide, N-(2-{7-[3-({8-[2-(acetylamino)ethyl]-2-naphthyl}oxy)propoxy]-1-naphthyl}ethyl)acetamide, N-(2-{7-[4-({8-[2-(acetylamino)ethyl]-2-naphthyl}oxy)butoxy]-1-naphthyl}ethyl)acetamide, N-[2-(7-{[6-({8-[2-(acetylamino)ethyl]-2-naphthyl}oxy)hexyl]oxy}-1-naphthyl)ethyl]acetamide, N-[2-(7-{[5-({8-[2-(acetylamino)ethyl]-2-naphthyl}oxy)pentyl]oxy}-1-naphthyl)ethyl]-acetamide, N-[2-(7-{[8-({8-[2-(acetylamino)ethyl]-2-naphthyl}oxy)octyl]oxy}-1-naphthyl)ethyl]acetamide, N-[2-(7-{[10-({8-[2-(acetylamino)ethyl]-2-naphthyl}oxy)decyl]oxy}-1-naphthyl)ethyl]acetamide and N-(2-{7-[4-({8-[2-(acetylamino)ethyl]-7-methoxy-2-naphthyl}oxy)butoxy]-2-methoxy-1-naphthyl}ethyl)acetamide, and addition salts thereof with a pharmaceutically/acceptable acid or base.

15. A compound of formula (I) according to claim 1 which is selected from N-[2-(7-{2-[2-({8-[2-(acetylamino)ethyl]-2-naphthyl}oxy)ethoxy]ethoxy}-1-naphthyl)ethyl] acetamide and its addition salts with a pharmaceutically/acceptable acid or base.

16. A compound of formula (I) according to claim 1 which is selected from N-(2-{7-[4-({8-[2-(2-furoylamino)ethyl]-2-naphthyl}oxy)butoxy]-1-naphthyl}ethyl)-2-furamide, 2-bromo-N-[2-(7-{4-[(8-{2-[(bromoacetyl)amino]ethyl}-2-naphthyl)oxy]butoxy}-1-naphthyl)ethyl]acetamide, N-[2-(7-{4-[(8-{2-[(cyclopropylcarbonyl)amino]ethyl}-2-naphthyl)oxy]butoxy}-1-naphthyl)ethyl] cyclopropanecarboxamide and N-(2-{7-[4-({8-[2-(3-butenoylamino)ethyl]-2-naphthyl}oxy)butoxy]-1-naphthyl}ethyl)-3-butenamide, and addition salts thereof with a pharmaceutically/acceptable acid or base.

17. A compound of formula (I) according to claim 1 which is selected from N-(2-{7-[4-({8-[2-(acetylamino)ethyl]-5,6,7,8-tetrahydro-2-naphthalenyl}oxy)butoxy]-1,2,3,4-tetrahydro-1-naphthalenyl}ethyl)acetamide, its enantiomers and diastereoisomers, and addition salts thereof with a pharmaceutically/acceptable acid or base.

18. A compound of formula (I) according to claim 1 which is selected from N-{2-[5-(4-{[3-[2-(acetylamino)ethyl]-1-(phenylsulphonyl)-1H-indol-5-yl]oxy}butoxy)-1-(phenyl-sulphonyl)-1H-indol-3-yl]ethyl}acetamide and N-(2-{5-[4-({3-[2-(acetylamino)ethyl]-1H-indol-5-yl}oxy)butoxy]-1H-indol-3-yl}ethyl)acetamide, and addition salts thereof with a pharmaceutically/acceptable acid or base.

19. A compound of formula (I) according to claim 1 which is selected from N-(2-{5-[4-({3-[2-(acetylamino)ethyl]-1-benzofuran-5-yl}oxy)butoxy]-1-benzofuran-3-yl }ethyl) acetamide and N-(2-{5-[4-({3-[2-(acetylamino)ethyl]-1-benzothien-5-yl}oxy)butoxy]-1-benzothien-3-yl}ethyl) acetamide, and addition salts thereof with a pharmaceutically/acceptable acid or base.

20. A compounds of formula (I) according to claim 1 which is N-(2-{5-[4-({3-[2-(acetylamino)ethyl]-1-methyl-1H-pyrrolo[3,2-b]pyridin-5-yl}oxy)butoxy]-1-methyl-1H-pyrrolo[3,2-b]pyridin-3-yl}ethyl)acetamide and N-(2-{5-[4-({3-[2-(acetylamino)ethyl]-1-methyl-1H-pyrrolo[3,2-b]pyridin-5-yl}oxy)propoxy]-1-methyl-1H-pyrrolo[3,2-b]pyridin -3-yl}ethyl)acetamide, and addition salts thereof with a pharmaceutically/acceptable acid or base.

21. A compound of formula (I) according to claim 1 which is selected from N-[2-(7-{8-[2-(acetylamino)ethyl]-2-naphthyl}-1-naphthyl)ethyl]acetamide, and addition salts thereof with a pharmaceutically/acceptable acid or base.

22. A compound of formula (I) according to claim 1 which is selected from N-{2-[5-{3-[2-(acetylamino)ethyl]-1H-indol-3-yl}-1H-indol-3-yl]ethyl}acetamide, and addition salts thereof with a pharmaceutically/acceptable acid or base.

23. A method for treating a living body afflicted with disorder of the melatoninergic system comprising the step of administering to the living body an amount of a compound of claim 1 together with one or more pharmaceutically/acceptable excipients or vehicles which is effective for the alleviation of said disorder.

24. A pharmaceutical composition useful for treating melatoninergic disorders comprising, as active principle, an effective amount of a compound as claimed in claim 1, together with one or more pharmaceutically/acceptable excipients or vehicles.

* * * * *

UNITED STATES PATENT AND TRADEMARK OFFICE
CERTIFICATE OF CORRECTION

PATENT NO. : 6,319,930 B1
DATED : November 20, 2001
INVENTOR(S) : Daniel Lesieur et al.

It is certified that error appears in the above-identified patent and that said Letters Patent is hereby corrected as shown below:

Column 29,

Line 42,    "_____" should be "= = = = =".

Line 63,    "_____" should be "= = = = =".

Column 30,
Line 28, "methyl" should be -- ethyl --. (2nd occurrence)

Column 31,
Lines 47 & 51-52, "pharmaceutically/acceptable" should be
-- pharmaceutically - acceptable --

Column 32,
Lines 1-55, "pharmaceutically/acceptable" should be
-- pharmaceutically - acceptable --
Line 28, insert -- selected from -- after "which is".

Signed and Sealed this

Seventeenth Day of February, 2004

JON W. DUDAS
*Acting Director of the United States Patent and Trademark Office*